Figure 1:
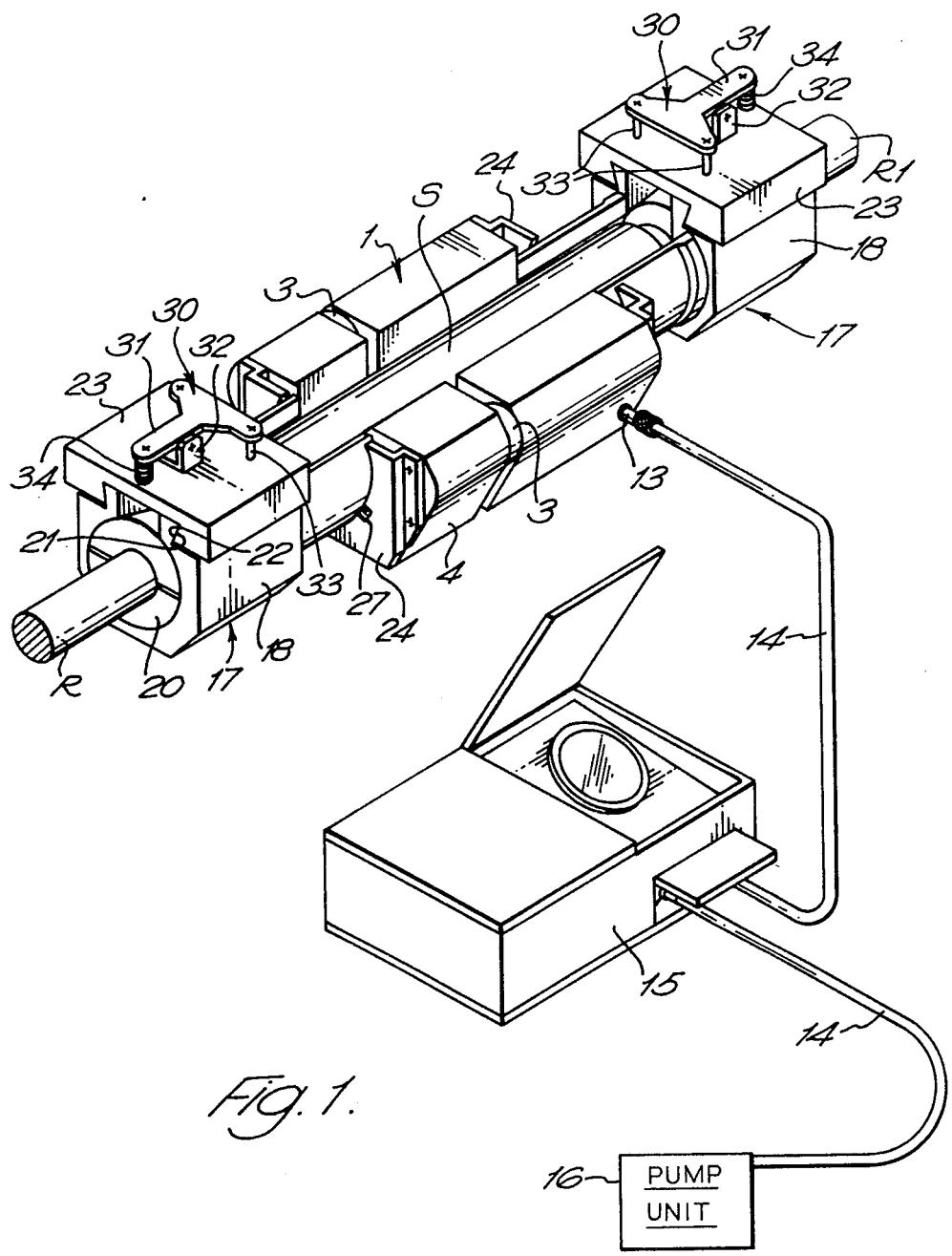

United States Patent [19]
Edwards

[11] 3,954,005
[45] May 4, 1976

[54] PROOF LOADING APPARATUS FOR TESTING ROD-LIKE ARTICLES

[75] Inventor: Hugh Jeremy Willis Edwards, Guiseley, England

[73] Assignee: CCL Systems Limited, Surbiton, England

[22] Filed: Mar. 10, 1975

[21] Appl. No.: 556,944

[30] Foreign Application Priority Data
Mar. 20, 1974 United Kingdom............... 12346/74

[52] U.S. Cl.................................. 73/103; 254/29 A
[51] Int. Cl.²........................................... G01L 5/08
[58] Field of Search ............... 73/103, 95.5, 95, 97, 73/143, 160; 254/29 A, 135 R

[56] References Cited
UNITED STATES PATENTS
1,341,431  5/1920  Morrow ................................ 73/103
2,884,986  5/1959  Heldenbrand ..................... 73/97 X

*Primary Examiner*—Jerry W. Myracle
*Attorney, Agent, or Firm*—Baldwin, Wight & Brown

[57] ABSTRACT

Proof Loading apparatus for the non-destructive testing of rod-like articles, characterized in that it comprises a jack housing (1) incorporating at least one hydraulic ram (2, 3), first and second gripping devices (17) arranged at opposite ends of the jack housing and being axially movable, on operation of the ram, relative to one another, wherein the jack housing (1) and the gripping devices (17) are of generally C-shaped cross-section.

11 Claims, 3 Drawing Figures

PROOF LOADING APPARATUS FOR TESTING ROD-LIKE ARTICLES

This invention relates to proof loading apparatus for the non-destructive testing or rod-like articles. In particular, the invention is concerned with the in situ testing of spliced reinforcing bars of the kind used in reinforced concrete structures.

Mechanically swaged joints in place of conventional lapped and welded joints for joining together, in end-to-end relationship, reinforcing bars, is a comparatively new method of jointing and there is a certain reluctance on the part of engineers to use swaged joints because there is no way of seeing whether the joint has been properly made.

Furthermore, it is the usual practice that the joining together of reinforcing bars be carried out on the site using portable swaging apparatus. This means that any testing of the finished joint must also be carried out on the site invariably with the bars in situ.

It is among the objects of the present invention to provide proof testing apparatus which is such as to satisfy the design engineer that a sound connection has been made, thereby promoting confidence in the use of mechanically swaged joints.

According to the present invention, there is provided proof loading apparatus for the non-destructive testing of rod-like articles, which comprises a jack housing incorporating at least one hydraulic ram, first and second gripping devices arranged at opposite ends of the jack housing and being axially movable relative to one another, wherein the jack housing and the gripping devices are of generally C-shaped cross-section.

According to a more particular aspect of the present invention, there is provided proof loading apparatus for the non-destructive testing of rod-like articles, which comprises a jack housing, a pair of spaced apart cylinders formed in the jack housing, a piston member arranged in each of the cylinders both of which pistons are connected to a common movable beam member, and first and second barrel type gripping devices which respectively are fixed to, or capable of being attached to, the jack housing and the movable beam member and being movable relative to one another, wherein the jack housing, the movable beam member and the barrels of the gripping devices are of generally C-shaped cross-section.

According to a further feature of the invention, in order to reduce the size of the barrel of each gripping device, opposite edges thereof are inter-connected by means of a removable wedge plate.

Figure 2:
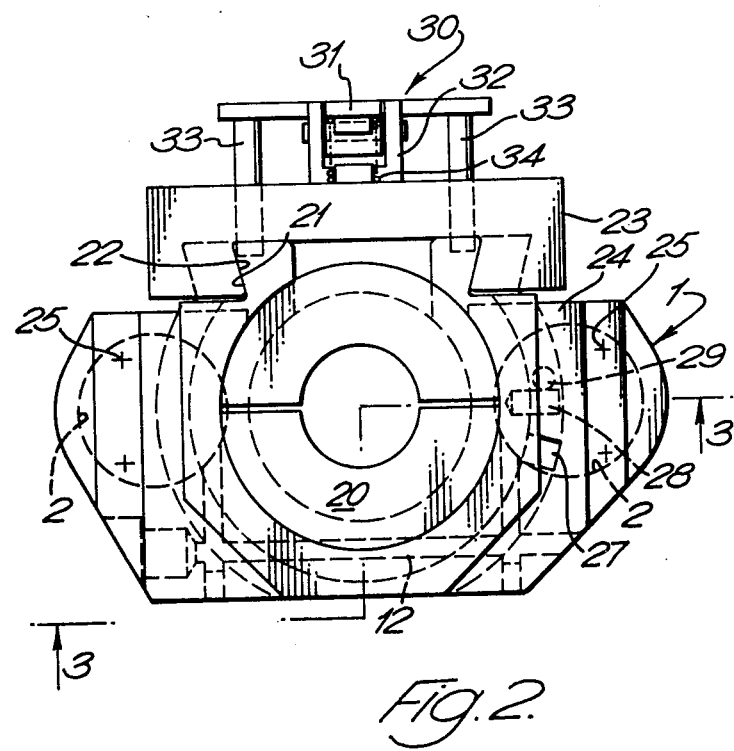
Figure 3:
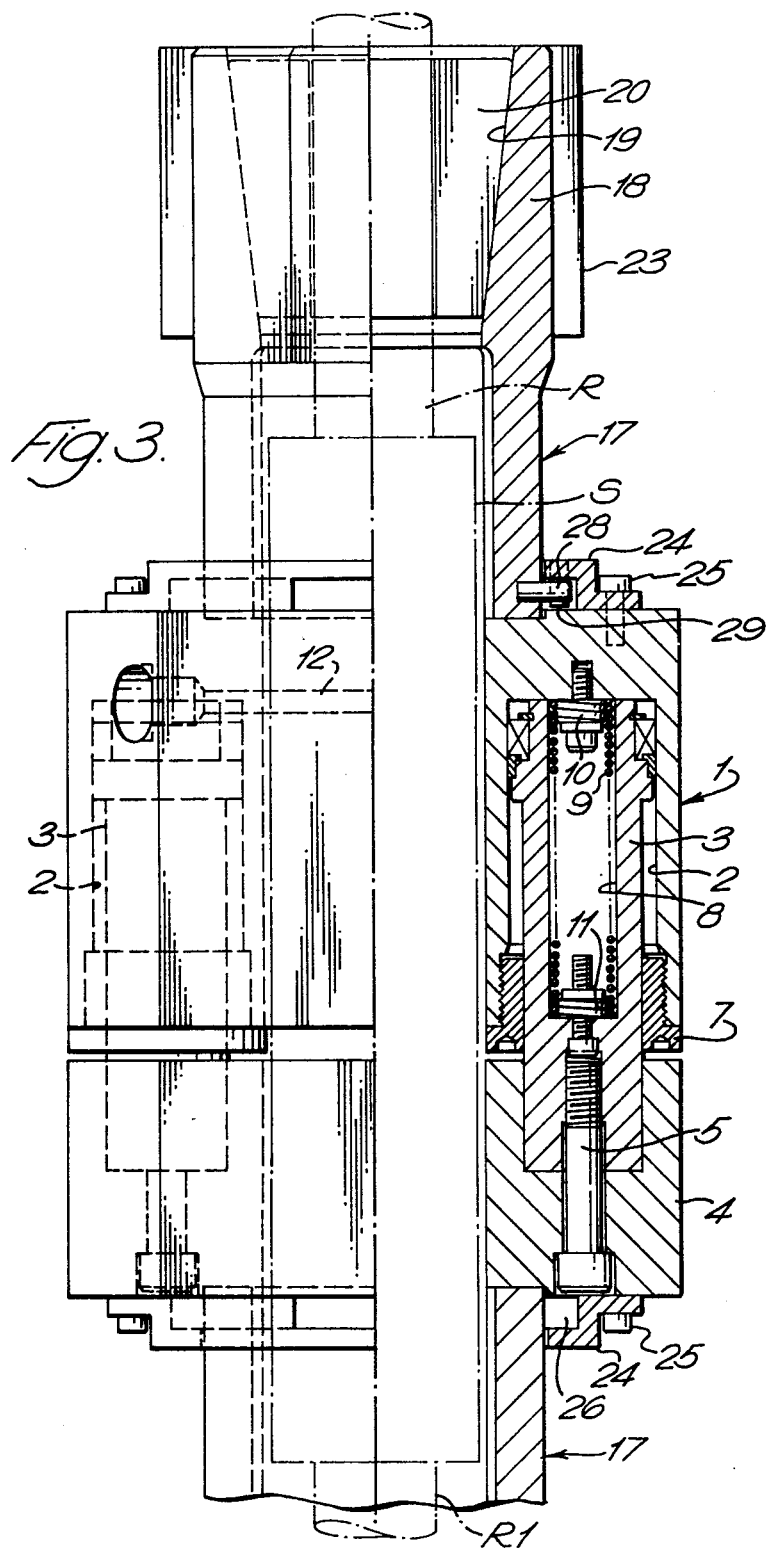

The invention is illustrated by way of example in the accompanying drawings in which, FIG. 1 is a perspective view of one embodiment of proof loading apparatus according to the invention, FIG. 2 is an end elevation corresponding to FIG. 1, and FIG. 3 is a section, partly in elevation, on the line 3 — 3 of FIG. 2.

Referring to the drawings, the proof loading apparatus comprises a jack housing 1 of generally C-shaped cross-section having formed therein adjacent the end of each arm thereof, at diametrically opposite positions, a cylinder 2. Each of the cylinders 2 has received therein a piston member 3, both piston members being fixed to a movable beam member 4 by means of screwed bolts 5. An end cap 7 is provided in the end of each cylinder 2.

The piston members 3 are each provided with a central bore 8 to receive a tension spring 9 which is anchored, at one end, to the jack housing 1 by means of a spring retainer 10 and, at its other end, to the piston member 3 by means of a spring retainer 11.

Passageways 12 are formed in the jack housing 1 to communicate with both cylinders 2, the passageways also being capable, via an inlet connection 13 and flexible pipes 14, of being placed in communication with a pressure gauge and control case 15 and via a pump unit 16, with a source of hydraulic pressure.

Thus, it will be seen that the jack is extended by hydraulic pressure and is returned to its inoperative position by means of the tension springs 9.

Attached to the jack housing 1 and the movable beam member 4 respectively is a barrel type gripping device 17. Each gripping device 17 comprises a barrel 18 of generally C-shaped cross-section the outer end portion of which is formed with a frusto-conical inner periphery 19 to receive a two or more part annular gripping wedge 20.

The extreme end of the arms of the C-shaped barrel 17 are formed with dovetail shaped surfaces 21 to co-act with correspondingly shaped surfaces 22 formed on a detachable wedge plate 23. Thus, in use, the wedge plate 23 slidably engages the arms of the barrel 18 and serves to prevent any tendency for the arms to move apart due to pressure exerted via the gripping wedge 20.

As indicated above, the gripping devices 17 are detachably secured respectively to the jack housing 1 and the movable beam member 4. For this purpose a barrel retainer plate 24 is fixed, as by bolts 25, to the housing 1 and the beam member 4 to present an annular cavity 26. The inner peripheral edge of the plate 24 is formed with a cut-out opening 27 to permit a radially extending pin 28 provided near the end of the barrel 18 to pass therethrough. In order to attach a gripping device 17 to the housing 1 and the beam member 4, the barrel 18 is positioned in the opening of the plate 24 by passing the pin 28 through the cut-out opening 27. The barrel is then angularly turned about its longitudinal axis so that the pin 28 enters the cavity 26 and holds the barrel in position. To provide correct alignment of the barrel, a stop pin 29 is provided to project into the cavity 26 to be engaged by the pin 28.

In order to retain the wedge plates 23 in position on the ends of the arms of the co-acting barrels 18, each wedge plate is provided with a spring loaded retaining device 30. The device 30 comprises a T-shaped arm 31 which is hingedly mounted on a bracket 32 fixed to the plate 23. The ends of the cross-bar of the T each have a locating pin 33 which passes through a hole in the plate 23 and into co-acting holes in the ends of the arms of the barrel 18. A compression spring 34 is positioned between the tail of the T and the surface of the plate 23 to bias the pins 33 into engagement with their co-acting holes. Thus, in order to remove plate 23, the tail of the T is depressed and the plate is slid relative to the arms of the barrel 18. In order to replace the plate 23, the tail of the T is again depressed and the plate is slid onto the ends of the arms and then released. Further sliding movement will result in the pins 33 automatically falling into the co-acting holes in the arms of the barrel 18 and thereby position and retain the plate 23.

The operation of the apparatus will now be described with reference to carrying out a test to ascertain whether a spliced joint 5 between two reinforcing bars R and R1 is sound. Spliced joints between reinforcing bars are usually made on site and therefore the apparatus is portable so that it can effect the testing operation with the reinforcing bars in situ.

Firstly, the wedge plates 23 and the gripping wedges 20 are removed and the apparatus is offered up to the joined reinforcing bars R and R1 so that the mechanical splice 5 thereof is positioned within the jack housing 1, and so that the reinforcing bars extend through the barrels 18 of the respective gripping devices 17. The wedge plates 23 are then slid into position and the elements of the gripping wedges 20 placed around the bars R and R1 and fitted into the portions 19 of the barrels 18. Hydraulic pressure is applied to extend the jack thus causing the gripping devices 17 to tightly engage the bars and to apply tension to them relative to the mechanical splice 5. When the desired testing pressure is reached, the hydraulic pressure is released and the jack is returned to its inoperative position under the action of the springs 9 at which time the apparatus can be removed.

It will be realized that the apparatus according to the invention has the following advantages:

1. The C-shaped formation thereof enables it to be placed in position at any point along a rod-like member. 2. The provision of two diametrically oppositely positioned pistons, as distinct from a single piston on one side thereof, provides uniform tension and enables the size of the apparatus to be as small as possible thereby enabling it to be used on closely spaced reinforcing bars. 3. The provision of the wedge plates 23 enables the gripping devices 17 to be as small as possible.

I claim:

1. Proof loading apparatus for the non-destructive testing of rod-like articles, said apparatus being of lesser length than articles for which it is particularly adapted to test and comprising a jack housing, at least one hydraulic ram arranged in said jack housing, first and second gripping devices arranged at opposite ends of said jack housing said gripping devices being axially movable, on operation of said ram, relative to one another, wherein said jack housing and said gripping devices are of generally C-shaped cross-section along their length.

2. Proof loading apparatus for the non-destructive testing of rod-like articles, which comprises a jack housing, a pair of spaced apart cylinders formed in said jack housing, a piston member arranged in each of said cylinders both of said piston members being connected to a common movable beam member, and first and second barrel type gripping devices connected respectively to one end of said jack housing and said movable beam member so as to be axially movable, on operation of said piston members, relative to one another, wherein said jack housing, said movable beam member and the barrels of said gripping devices are of generally C-shaped cross-section.

3. Apparatus as claimed in claim 2, in which said cylinders are positioned, in diametrically opposite positions of said barrels of said gripping devices, adjacent the free ends, as viewed in cross-section, of said jack housing.

4. Apparatus as claimed in claim 3, in which means are provided on said jack housing and said movable beam member to detachably receive said gripping devices.

5. Apparatus as claimed in claim 4, in which said means comprise barrel retainer plates which are bolted in position, each of said plates providing an annular cavity to receive a retainer pin arranged adjacent the end of the barrel of the co-acting gripping device.

6. Apparatus as claimed in claim 2, in which the free ends, as viewed in cross-section, of said barrel of each of said gripping devices is formed with a lengthwise tapered portion, and a wedge plate having a co-acting dovetail groove formed therein, each wedge plate being mounted on a respective one of said barrels with said groove receiving said tapered portion.

7. Apparatus as claimed in claim 6, in which means are provided for locating and locking said wedge plate relative to said free ends of said barrel of said gripping device.

8. Apparatus as claimed in claim 7, in which said locating and locking means comprise a T-shaped arm hingedly mounted on said wedge plate and having projections which extend through co-acting holes in said wedge plate and the arms of said barrel.

9. Apparatus as claimed in claim 2, in which said piston members are single acting and there is a common source of fluid pressure connected to said piston members for operating said piston members.

10. Apparatus as caimed in claim 9, in which each cylinder has a base and each piston member has an axially extending cavity, and a tension spring is housed in the cavity in each of said piston members, ends of each spring being anchored to the base of a respective cylinder and to a respective piston member to provide for return movement of the respective piston member.

11. Apparatus as claimed in claim 10, in which spring retaining elements are provided to anchor the ends of said spring.

* * * * *